United States Patent [19]

Olive et al.

[11] Patent Number: 5,423,870
[45] Date of Patent: Jun. 13, 1995

[54] RATE RESPONSIVE CARDIAC PACEMAKER

[75] Inventors: Arthur L. Olive, Stacy; Rodney W. Salo, Fridley, both of Minn.

[73] Assignee: Cardiac Pacemakers, Inc., St. Paul, Minn.

[21] Appl. No.: 155,482

[22] Filed: Nov. 22, 1993

[51] Int. Cl.⁶ .............................................. A61N 1/36
[52] U.S. Cl. .......................................... 607/18; 607/9
[58] Field of Search ........................... 607/18–24

[56] References Cited

U.S. PATENT DOCUMENTS

| | | | |
|---|---|---|---|
| 4,884,576 | 12/1989 | Alt | 607/24 |
| 4,945,909 | 8/1990 | Fearnot et al. | 607/19 |
| 4,966,146 | 10/1990 | Webb et al. | 607/22 |
| 5,088,488 | 2/1992 | Markowitz et al. | 607/22 |

FOREIGN PATENT DOCUMENTS

| | | | |
|---|---|---|---|
| 8505279 | 12/1985 | WIPO | 607/21 |
| 9320889 | 10/1993 | WIPO | 607/18 |

OTHER PUBLICATIONS

"One-Year Follow-Up of Automatic Adaptation of the Rate Response Algorithm of the QT Sensing Rate Adaptive Pacemaker" by M. W. Baig et al PACE, vol. 14, pp. 1598-1605.

*Primary Examiner*—William E. Kamm
*Assistant Examiner*—Marianne Parker
*Attorney, Agent, or Firm*—Haugen and Nikolai

[57] ABSTRACT

A cardiac pacemaker having an automatic pulse rate response gain factor responsive to at least one cardiac-related physiological characteristic of a patient. The pacemaker includes a rate controller that comprises a detector for detecting a plurality of individual measurements of at least one physiological characteristic over each of a plurality of pre-determined time periods, with each of the individual measurements being an average of values detected over each of a respective multiple number of incremental time periods occurring within each of the pre-determined time periods. The pacemaker saves the highest measurement from one incremental time period of each of several consecutive pre-determined time periods, and these highest measurements are averaged. Thereafter, the rate controller adjusts the rate response gain factor or slope of the pulse rate in relation to the physiological characteristic measurement and a pre-determined target pulse rate. In a preferred embodiment, two physiological characteristics are measured, with high values averaged of only one characteristic when that characteristic exceeds a threshold level of the other characteristic. One embodiment is pulse rate responsive to minute volume measurement in combination with accelerometer measurement, with accelerometer measurement requiring a threshold value over an increment of time prior to minute volume recordation for input toward rate response gain factor.

21 Claims, 3 Drawing Sheets

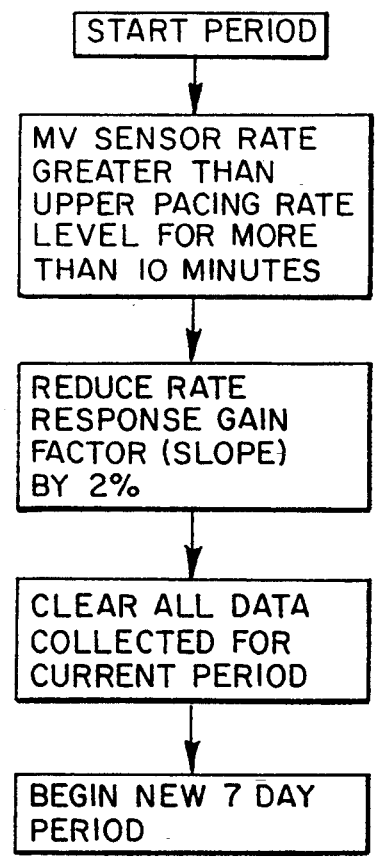

RATE RESPONSIVE CARDIAC PACEMAKER

BACKGROUND OF THE INVENTION

This invention relates in general to rate responsive cardiac pacemakers, and in particular to a pacemaker whose rate response gain factor or slope adjustment is automatically provided in relation to cardiac-related physiological characteristics of a patient.

Rate response gain factor or slope adjustment is an important aspect in cardiac pacemaker operation as physiological consideration of a patient becomes more and more integrated with treatment modes. Further, because of the vagaries among patients, pre-set and solely manually adjustable arbitrary settings in a pacemaker device to regulate pulse delivery rates are not practical or in the best interest of the patient. Individual testing sessions for each patient, while perhaps desirable, are not practical because of time and money investments needed for such a program.

It is, of course, obvious that increased patient activity requires increased pulsed delivery from a pacemaker. However, it is important that this increased pulse velocity have a physiological relationship to its need. Measurements that have cardiac relevance to pulse velocity requirements include minute volume, general patient activity which can be equivocated to accelerometer response in a so equipped pacemaker, right ventricle stroke volume, right ventricular pressure, blood oxygen level, central venous blood temperature, and the like.

It is therefore a primary object of the present invention to provide a cardiac pacemaker which captures peak values of at least one cardiac-related physiological measurement over a consecutive preset number of time segments and then provides for automatic adjustment of the rate response slope.

It is a further object of the present invention to provide a cardiac pacemaker which compares peak values of two separate physiological measurements wherein one such measurement must reach a preset threshold level before peak values of the other measurement are captured over a number of present time segments for use in pulsing rate adjustments.

Another object of the present invention is to provide a cardiac pacemaker which compares minute volume measurements to patient activity measurements and captures peak minute volume levels coincident to significant patient activity levels as exemplified by accelerometer values exceeding a threshold level over a plurality of separate time segments.

It is a further object of the present invention to provide a cardiac pacemaker which captures the minute volume ratios of each peak minute volume measurement and thereafter averages these ratios over the plurality of time segments.

Yet another object of the present invention is to provide a cardiac pacemaker having control signal generating means for adjusting a rate response gain factor of the pacemaker such that peak minute volume ratios achieve a pre-determined heart-rate target value during periods of peak patient activity.

These and other objects of the present invention will become apparent throughout the description which now follows.

SUMMARY OF THE INVENTION

The present invention is a cardiac pacemaker having pulse generation means which include pulse rate control means that comprise, first of all, means for detecting a plurality of measurements of at least one cardiac-related physiological characteristic of a patient over each of a plurality of pre-determined periods of time, with each of the individual measurements being over respective multiple incremental periods of time occurring within each of the pre-determined periods of time. During each pre-determined period of time, only the data from one incremental period of time is saved, with such saved data being the highest average value obtained in an incremental period occurring over the pre-determined period. The pacemaker further comprises means for saving the highest measurement during each of the plurality of pre-determined periods of time. Means are present to thereafter average these saved measurements over a plurality of periods of time, after which control means adjust a rate responsive gain factor or slope of the stimulating pulses of the pacemaker in relation to the physiological characteristic base value and a pre-determined pacing target value for these averaged measurement values. Preferably, the pre-determined period of time is 24 hours, while each of the multiple incremental time periods within the 24-hour period is about one to 10 minutes, and the plurality of pre-determined periods of time over which averages are calculated is seven days. During each 24-hour period, only the averaged data from one incremental one-to-ten minute period is saved, with such saved data being the highest obtained in all of the incremental periods occurring over that 24-hour period. The preferred pre-determined target pacing rate derived from physiological characteristic values for the averaged measurements is about 75% of the upper pacing rate limit of the pacemaker. Rate response gain factor adjustments should be incrementally moderate, and preferably should be no more than about a four percent change per adjustment. Measured physiological characteristics can be chosen from the group consisting of minute volume, general patient activity as reflected by an accelerometer response, right ventricle stroke volume or pressure, blood oxygen level, central venous blood temperature, and the like.

While only a single physiological characteristic can be measured for slope adjustment of the pacemaker, it is preferable to have two physiological characteristics simultaneously measured, with one of these measurements having a threshold level which must be reached before measurement values of the second characteristic are captured for subsequent averaging. Thus, in a preferred embodiment, the rate control means comprise, first of all, an accelerometer for detecting a plurality of individual activity level measurements of a patient as described above. Additional means are provided for detecting a plurality of individual minute volume ratio measurements coincidentally with the individual activity level measurements over identical incremental periods of time. The pacemaker further comprises means for saving the highest minute volume ratio measurement during each of the pre-determined time periods wherein the aforementioned activity level measurements exceed a pre-determined threshold value. Thus, when two physiological characteristics are measured, one of the characteristics can function as a gate or qualifier whose value must exceed a threshold magnitude before a measurement of the second physiological characteristic is captured and included in determining subsequent slope modification.

BRIEF DESCRIPTION OF THE DRAWINGS

FIG. 4 is an operational chart of the pacemaker of the present invention showing an alternate operation thereof related to excess minute volume values of a patient.

DETAILED DESCRIPTION OF A PREFERRED EMBODIMENT

The preferred embodiment of the present invention comprises a cardiac pacemaker which provides pulse generating rate control based upon an algorithm which correlates minute volume sensor values occurring simultaneously with accelerometer values to minute volume ratio values over increments of time within a finite period of time. In particular, the preferred pacemaker monitors minute volume (MV) and accelerometer (ACCEL) values constantly, and responds by saving the highest minute volume sensor rate over a one to 10 minute time increment occurring in a 24-hour period when the minute volume sensor rate is accompanied by accelerometer activity which denotes patient activity above the threshold value of the accelerometer. Thus, the preferred embodiment requires simultaneous heightened general activity and heightened minute volume value before minute volume value is analyzed for possible inclusion in a subsequent adjustment of pulsing rate. Increased accelerometer output level must be maintained for a minimum time, but less than a maximum time. In the preferred embodiment, this time span is between one and 10 minutes. Concurrent with the above is the computation of the minute volume ratio which is, of course, defined as current minute volume sensor rate value divided by minute volume base value. At the end of each 24-hour period, the pacemaker saves the highest or peak average minute volume sensor rate value and minute volume ratio value occurring during one one-to-ten minute increment of the 24-hour period, discards all other minute volume sensor rate and ratio values for the 24-hour period, and resets to repeat this 24 hour process. At the end of a seven day period, all of the peak values of the minute volume sensor rates and ratio values are averaged and the pacing rate response gain factor or slope is adjusted as required to more accurately reflect pacing demand and to achieve a preferred target pacing rate which may be set at 75% of the maximum pacing rate attainable. The 24-hour and seven day capture and computation process is continuously subsequently repeated to thereby continuously adjust pacing rate in relation to minute volume sensor rate as coupled with accelerometer activity.

Figure 1:
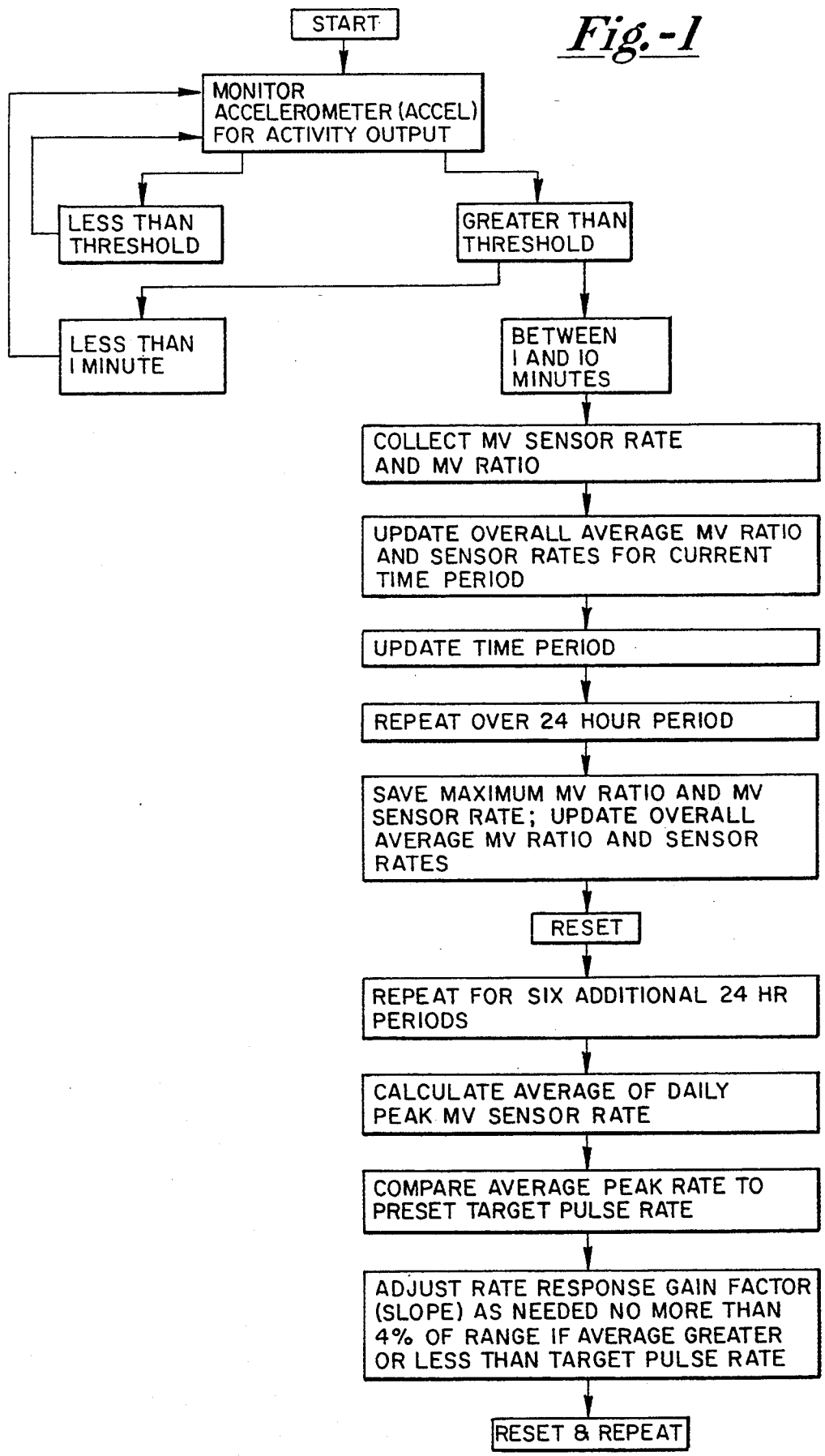
FIG. 1 is an operational flow chart of a pacemaker of the present invention.

Reference is now made to FIG. 1 which illustrates the step- by-step process for each 24-hour period. Specifically, throughout each 24-hour period, the accelerometer and minute volume sensors are constantly monitored. When the accelerometer is active (above threshold) for one to 10 minute increments, the minute volume sensor rate and minute volume ratio are collected for each of these increments and the respective averages of these two values are continuously updated throughout the 24-hour period. At the conclusion of the 24-hour period, the peak minute volume sensor rate and peak minute volume ratio averages over one increment are saved, and, after resetting, the process is repeated for six additional 24-hour periods. At the end of the seven days, the resulting seven daily peak minute volume sensor rates and minute volume ratio values are averaged. If the weekly sensor rate average is above or below 75% of the maximum pre-set pulsing rate of the pacemaker, the pulsing rate response curve is adjusted a maximum of 4% of its range to thereby bring the averaged peak minute volume sensor values closer to 75% of the maximum pulsing rate. No pulsing rate response change is provided where the minute volume ratio is less than 1.2 or some other pre-programmed value.

Figure 2:
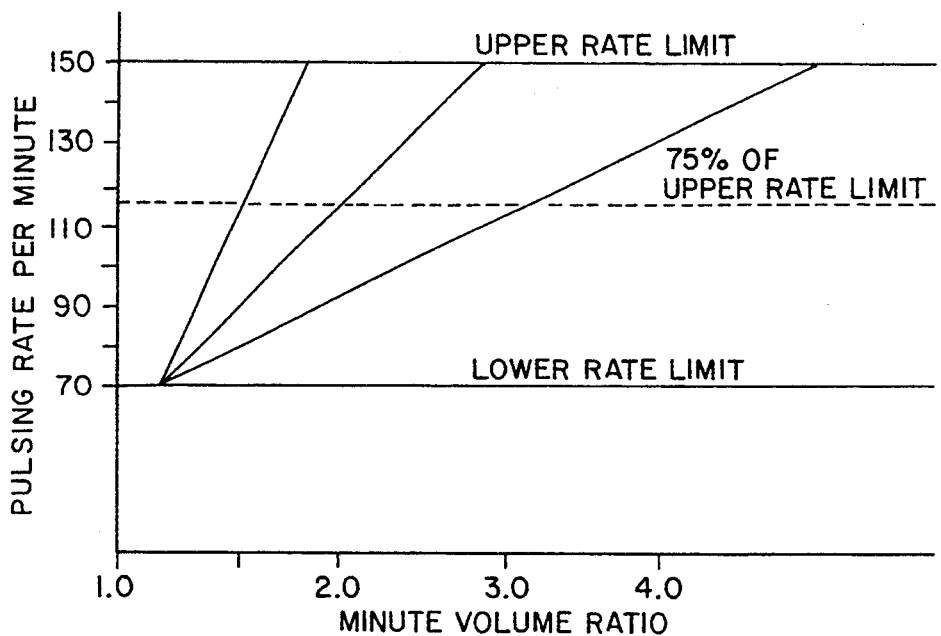
FIG. 2 is a graph showing the relationship between pulsing rate per minute of the pacemaker of the present invention and minute volume ratio of a patient.
Figure 3:
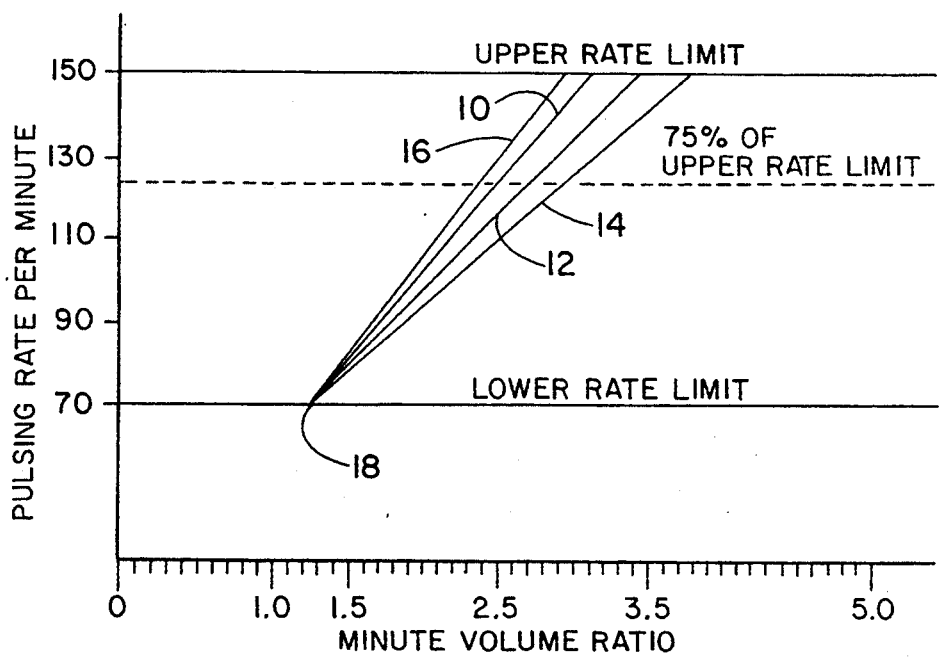
FIG. 3 is a graph similar to that of FIG. 2 showing the relationship between pulsing rate per minute of the pacemaker of the present invention and minute volume ratio.

FIG. 2 illustrates graphically the relationship between pulsing rate and minute volume ratio value. As there shown, after the ratio reaches 1.2, the lower pulsing rate limit (shown here as 70 per minute) is affected. Because the target pulsing rate is 75% of the upper pulsing rate limit (here shown as 150 per minute), the minute volume ratio determines the pulsing rate delivered. FIG. 3 also illustrates the relationship between pulsing rate and minute volume ratio, and additionally shows slope change as described above. In particular, line 10 shows a pre-set rate response gain factor or slope whereby, on an arbitrary scale of 0 to 5.0 which expresses minute volume ratio, 2.5 is chosen as the point where peak minute volume is at 75% of the upper pulsing rate per minute. Line 12 exemplifies an incremental adjustment to the initial setting of line 10, and represents a slope adjustment wherein the 75% pulsing rate velocity now has a value of 2.7. This 0.2 point change represents 4% of the minute volume sensor output range, with 0.2 point being the preferred change increment to be made after each seven day period where the peak average minute volume sensor rate output is below 75% of the upper pulsing rate limit. Line 14 exemplifies a subsequent adjustment which could occur seven days after the first slope adjustment occurs. It is to be noted that the point 18 of initial rise of the slope does not change, thereby keeping the rate increase threshold a constant. Finally, line 16 in the graph of FIG. 3 exemplifies a decremental adjustment to the slope when a seven day peak minute volume sensor rate average exceeds 75% of the upper pulsing rate limit. While incremental changes of 0.2 point (4%) are preferred, as in line 12, decremental changes are preferably limited to 0.1 point (2%).

FIG. 4 illustrates an additional response characteristic which can be included as part of the preferred embodiment. This characteristic is a "bail out" feature which adjusts the pulsing rate to force a rapid change response if the minute volume sensor rate output remains above the upper pulsing rate limit for a preset length of time. In the preferred embodiment this length of time is 10 minutes. When such a condition occurs, no matter at what point during the normal seven day data collection as shown in FIG. 1, the gain factor slope is immediately reduced by 0.1 point (2%), all data for that seven day period is cleared, and a new seven day period, as exemplified at "start" in FIG. 1, begins. In this manner, a rapid pacing response is imposed in response to a high rate from the minute volume sensor.

In use, the pacemaker instrument is implanted in the patient according to standard procedures as known in the art to thereby apply stimulating pulses to cardiac tissue. Likewise, minute volume sensor placement and minute volume activity data collection therefrom are as known in the art. The accelerometer is known in the art as is its data collection. Over a period of time, as described above, the pulsing rate provided by the instrument and as determined in view of minute volume sensor output and minute volume ratio is adjusted to approach an optimum level as required by each individual patient. While it is to be understood that gain factor or slope adjustment as described herein can be accomplished by utilizing output from the minute volume sensor means alone or the accelerometer output alone and still remain within the scope of the invention, the preferred embodiment hereof utilizes input from both the accelerometer and minute volume sensor as above described to thereby improve specificity of pacing requirements. Concurrently, and likewise within the scope of the present invention, time increment variables as well as time period variables can be programmed as desired and as may be beneficial to a patient as determined by a physician.

While an illustrative and presently preferred embodiment of the invention has been described in detail herein, it is to be understood that the inventive concepts may be otherwise variously embodied and employed and that the appended claims are intended to be construed to include such variation except insofar as limited by the prior art.

We claim:

1. In a cardiac pacemaker of the type having a pulse generating means for applying stimulating pulses to cardiac tissue, the pulse generating means including means for controlling the rate at which said stimulating pulses are applied, the improvement comprising in combination:
   (a) means for establishing an upper pulsing rate limit;
   (b) physiologic sensor means for producing an output characteristic of at least a first cardiac related physiological characteristic;
   (c) detector means for detecting a plurality of individual measurements of sensor rate output values of the physiologic sensor means over each of a plurality of pre-determined periods of time, with each of the individual measurements being an average of values detected over each of respective multiple incremental periods of time occurring within each of the pre-determined periods of time;
   (d) saver means for saving a highest one of said measurements occurring during one incremental period of time in each of the plurality of pre-determined periods of time;
   (e) averaging means for averaging the saved highest ones of said measurements over a plurality of periods of time to thereby yield an average physiological characteristic value;
   (f) adjuster means for adjusting, if necessary, a rate response gain factor of the stimulating pulses of the pacemaker in relation to a pre-determined physician specified target pulse rate for the averaged physiological characteristic value; and
   (g) resetting means responsive to operation of said adjuster means for clearing the detector means, saver means and averaging means.

2. The invention according to claim 1 wherein the physiological characteristics are selected from the group consisting of minute volume, general patient activity as reflected by an accelerometer response, right ventricle stroke volume, right ventricle pressure, blood oxygen level and central venous blood temperature.

3. The invention according to claim 1 including further detector means for detecting a plurality of individual measurements of a second physiological characteristic over each of a plurality of pre-determined periods of time, with each of the individual measurements being an average of values detected over each of respective multiple incremental periods of time occurring within each of the pre-determined periods of time, and with each of the measurements being performed coincidentally with the measurement of the first physiological characteristic over the same incremental period of time when the measurement of the first physiological characteristic is above a pre-determined threshold.

4. The invention according to claim 1 wherein the pre-determined period of time is 24 hours.

5. The invention according to claim 4 wherein the incremental period of time is between about one and 10 minutes.

6. The invention according to claim 5 wherein the plurality of pre-determined periods of time is seven days.

7. The invention according to claim 6 wherein the target pulse rate is about 75% of said upper rate pulsing limit of the pacemaker.

8. The invention according to claim 1 wherein the target pulse rate is about 75% of said upper rate pulsing limit of the pacemaker.

9. The invention according to claim 1 including an activation means which activates the adjuster means immediately when the cardiac-related physiological characteristic sensed by the physiologic sensor means has a sensor rate output value exceeding the upper pulsing rate limit for a pre-determined length of time, with said adjuster means immediately reducing the rate response gain factor by a pre-determined magnitude.

10. The invention according to claim 9 wherein the pre-determined length of time is 10 minutes.

11. The invention according to claim 10 wherein the rate responsive gain factor is reduced about two percent.

12. In a cardiac pacemaker of the type having a pulse generating means for applying stimulating pulses to cardiac tissue, the pulse generating means including means for controlling the rate at which said stimulating pulses are applied, the improvement comprising in combination:
   (a) means for establishing an upper pulsing rate limit for a patient;
   (b) activity level sensing means for sensing individual activity of the patient and producing a sensor rate output;
   (c) first detection means responsive to the activity level sensing means for detecting a plurality of individual sensor rate output values over each of a plurality of pre-determined periods of time, with each of the individual activity level measurements being an average of values detected over each of respective multiple incremental periods of time occurring within each of the pre-determined periods of time;
   (d) means for measuring minute volume values of the patient;
   (e) second detection means responsive to the minute volume measuring means for detecting a plurality of individual sensor rate output values for the patient over each of a plurality of pre-determine periods of time, with each of the minute volume measurements being an average of values detected over each of respective multiple incremental periods of time occurring within each of the pre-determined periods of time, and with each of the minute volume measurements being performed coincidentally with the individual activity level measurements over the same incremental period of time when said first detection means indicates an activity level that is above a pre-determined threshold activity level;

(f) saver means for saving a maximum value of minute volume measured during one incremental period of time in each of the plurality of pre-determined periods of time;

(g) averaging means for determining a minute volume sensor rate value and a minute volume ratio for each of said maximum minute volume measurements saved by said saver means and thereafter averaging these minute volume ratios over a plurality of periods of time, said minute volume ratio being a measured minute volume value divided by pre-determined minute volume base value for the patient;

(h) adjuster means for adjusting a rate response gain factor of the stimulating pulses of the pacemaker in relation to said minute volume sensor rate value and a physician-specified target value of a minute volume sensor rate value for these averaged minute volume ratios; and (j) resetting means responsive to the operation of said adjuster means for clearing the first and second detection means, saver means and averaging means.

13. The invention according to claim 12 wherein the first detection means is an accelerometer.

14. The invention according to claim 13 wherein the pre-determined period of time is 24-hours.

15. The invention according to claim 14 wherein the incremental period of time is between one and 10 minutes.

16. The invention according to claim 15 wherein the plurality of pre-determined periods of time is seven days.

17. The invention according to claim 16 wherein the target value of a minute volume target sensor rate value is 75% of said upper rate pulsing limit of the pacemaker.

18. The invention according to claim 12 wherein the target value of a minute volume target sensor rate value is about 75% of said upper rate pulsing limit of the pacemaker.

19. The invention according to claim 12 including an activation means which activates the adjuster means immediately when the sensor rate output of the minute volume measurements exceeds the upper pulsing rate limit for a pre-determined length of time, with said adjuster means immediately reducing the rate responsive gain factor a pre-determined magnitude.

20. The invention according to claim 19 wherein the pre-determined length of time is 10 minutes.

21. The invention according to claim 20 wherein the rate responsive gain factor is reduced about two percent.

* * * * *